(12) United States Patent
Wang et al.

(10) Patent No.: US 7,176,333 B2
(45) Date of Patent: *Feb. 13, 2007

(54) PROCESS FOR PREPARING 4-AMINODIPHENYLAMINE

(75) Inventors: Nongyue Wang, Cao County (CN);
Ruibiao Yu, Cao County (CN);
Xiaohui Mao, Cao County (CN);
Xiaogen Feng, Cao County (CN);
Qianwen Cheng, Cao County (CN)

(73) Assignee: Sinorgchem Company, Shandong, Shandong Province (CN)

( * ) Notice: Subject to any disclaimer, the term of this patent is extended or adjusted under 35 U.S.C. 154(b) by 80 days.

This patent is subject to a terminal disclaimer.

(21) Appl. No.: 10/882,677

(22) Filed: Jul. 2, 2004

(65) Prior Publication Data

US 2005/0065376 A1    Mar. 24, 2005

(30) Foreign Application Priority Data

| Jul. 4, 2003 | (CN) | ................. 03 1 48191 |
| Jul. 4, 2003 | (CN) | ................. 03 1 48194 |
| Jul. 4, 2003 | (CN) | ................. 03 1 48195 |
| Jul. 4, 2003 | (CN) | ................. 03 1 48196 |
| Jul. 4, 2003 | (CN) | ................. 03 1 48198 |
| Jul. 4, 2003 | (CN) | ................. 03 1 48200 |
| Jul. 4, 2003 | (CN) | ................. 03 1 48565 |
| Jul. 4, 2003 | (CN) | ................. 03 1 48566 |

(51) Int. Cl.
*C07C 209/60* (2006.01)

(52) U.S. Cl. ...................... 564/420; 564/421; 564/422; 564/423

(58) Field of Classification Search ...................... None
See application file for complete search history.

(56) References Cited

U.S. PATENT DOCUMENTS

| 4,102,926 A | 7/1978 | Usvyatsov et al. ......... 260/576 |
| 4,287,365 A | 9/1981 | Becker et al. .............. 564/422 |
| 4,313,002 A | 1/1982 | Symon et al. .............. 564/423 |
| 4,760,186 A | 7/1988 | Solodar ...................... 564/415 |
| 4,792,626 A | 12/1988 | Becher et al. .............. 564/422 |
| 5,117,063 A | 5/1992 | Stern et al. ................. 564/398 |
| 5,420,354 A | 5/1995 | Malz et al. ................. 564/423 |
| 5,453,541 A | 9/1995 | Stern et al. ................. 564/398 |
| 5,608,111 A | 3/1997 | Stern et al. ................. 564/398 |
| 5,739,403 A | 4/1998 | Reinartz et al. ............ 564/423 |
| 5,840,982 A | 11/1998 | Reynolds et al. ........... 564/423 |
| 5,925,791 A | 7/1999 | Buysch et al. .............. 564/416 |
| 5,932,768 A | 8/1999 | Ooms et al. ................ 564/416 |
| 5,973,206 A | 10/1999 | Laitinen ...................... 564/423 |
| 5,977,411 A | 11/1999 | DeVera ....................... 564/397 |
| 5,994,584 A | 11/1999 | Ooms et al. ................ 564/416 |
| 6,043,394 A | 3/2000 | Langer et al. .............. 564/423 |
| 6,137,010 A | 10/2000 | Joo et al. .................... 564/406 |
| 6,140,538 A | 10/2000 | Rains et al. ................ 564/416 |
| 6,316,673 B2 | 11/2001 | Giera et al. ................. 564/423 |
| 6,368,996 B1 | 4/2002 | Mu et al. .................... 502/301 |
| 6,388,136 B1 | 5/2002 | Beška et al. ................ 564/420 |
| 6,395,933 B1 | 5/2002 | Triplett, II et al. ......... 564/420 |
| 6,395,934 B1 | 5/2002 | Wegener et al. ............ 564/422 |
| 6,414,192 B1 | 7/2002 | Schelhaas et al. .......... 564/420 |
| 6,423,872 B2 | 7/2002 | Marion ....................... 564/422 |
| 6,495,723 B1 | 12/2002 | DeVera et al. .............. 564/419 |
| 6,583,320 B2 | 6/2003 | Triplett, II et al. ......... 564/420 |
| 6,680,280 B1 | 1/2004 | Birke et al. ................. 502/337 |
| 2002/0055652 A1 | 5/2002 | Schelhaas et al. .......... 564/434 |
| 2003/0088127 A1 | 5/2003 | Triplett et al. .............. 564/431 |

FOREIGN PATENT DOCUMENTS

| DE | 19709124.5 | 9/1998 |
| DE | 19734055.5 | 2/1999 |
| DE | 19810929.6 | 9/1999 |
| EP | 184914 | 6/1986 |
| EP | 784049 A1 | 7/1997 |

(Continued)

OTHER PUBLICATIONS

A. Wohl, Chemische Berichte, 34, pp. 2442-2459 (1901).
A. Wohl, Chemische Berichte, 36, pp. 4135-4138 (1903).
Fan, "4-Nitrosodiphenylamine," Organic Synthetic Dictionary, Beijing University of Science and Engineering Publication House, (Oct. 2003).

(Continued)

*Primary Examiner*—Brian Davis
(74) *Attorney, Agent, or Firm*—Venable LLP; Marina V. Schneller; Manni Li

(57) ABSTRACT

The present invention discloses a process for preparing 4-aminodiphenylamine, which process uses nitrobenzene and aniline as raw materials, a complex base catalyst as condensation catalyst and a powdery composite catalyst as hydrogenation catalyst, and comprises five process stages: condensation; separation I; hydrogenation; separation II; and refining. The process can be continuously carried out. By selecting a complex base catalyst to catalyze the condensation reaction and separating it prior to the hydrogenation, the problem that the complex base catalysts thermally decompose in the hydrogenation reaction is avoided, the selectable range of hydrogenation catalysts is largely enlarged so that it is possible to select cheaper hydrogenation catalyst, and the selection of production process and equipment is easier and further industrialization is easier. The complex base catalysts used in the present invention are inexpensive and have higher catalytic activity. The process can be carried out at mild conditions and can adapt to broad range of water content, by-product is less and conversion and selectivity are higher. The operational strength is low, no corrosive liquid is produced, and environment pollution is reduced. The purity of 4-aminodiphenylamine prepared can exceed 99 wt.-%, and the yield in the industrial production process can be over 95%.

35 Claims, 1 Drawing Sheet

FOREIGN PATENT DOCUMENTS

| | | |
|---|---|---|
| GB | 947082 | 1/1964 |
| GB | 2015998 A | 9/1979 |
| JP | 6306020 A | 11/1994 |
| JP | 6306021 A | 11/1994 |
| JP | 7-165682 A | 6/1995 |
| JP | 10-07627 A | 1/1998 |
| JP | 11-228506 A | 8/1999 |
| JP | 2001192701 A | 7/2001 |
| JP | 2001316337 A | 11/2001 |
| JP | 2002249467 A | 9/2002 |
| WO | WO 93/00324 | 1/1993 |
| WO | WO 94/25425 | 11/1994 |
| WO | WO 98/56751 | 12/1998 |
| WO | WO 99/28028 | 6/1999 |
| WO | WO 99/59956 | 11/1999 |
| WO | WO 00/51728 | 9/2000 |
| WO | WO 03/10126 | 2/2003 |

OTHER PUBLICATIONS

Wei et al., "New Method for Making p-Nitrodiphenylamine," Chemical Report, No. 10 (1996).

Zhu et al., "Study on Hydrogenation of Nitrodiphenylamine in Alkalescence System," Journal of Nanjing University of Technology, vol. 24, No. 6, pp. 48-51 (Nov. 2002).

Stern et al., "Direct Coupling of Aniline and Nitrobenzene: A New Example of Nucleophilic Aromatic Substitution for Hydrogen," J. Am. Chem. Soc. vol. 114, pp. 9237-9238 (1992).

Stern et al., "Eliminating Chlorine in the Synthesis of Aromatic Amines: New Routes Which Utilize Nucleophilic Aromatic Substitution for Hydrogen," New J. Chem., vol. 20, pp. 259-268 (1996).

Stern, "Chap. 11, Nucleophilic Aromatic Substitution for Hydrogen," ACS Symposium Series 577, Benign by Design (Aug. 1993).

Dickneider, "A Green Chemistry Module," website printout of Nov. 2003, http://academic.scranton.edu/faculty/CANNM1/advancedorganic/advancedorganicmodule.htm.

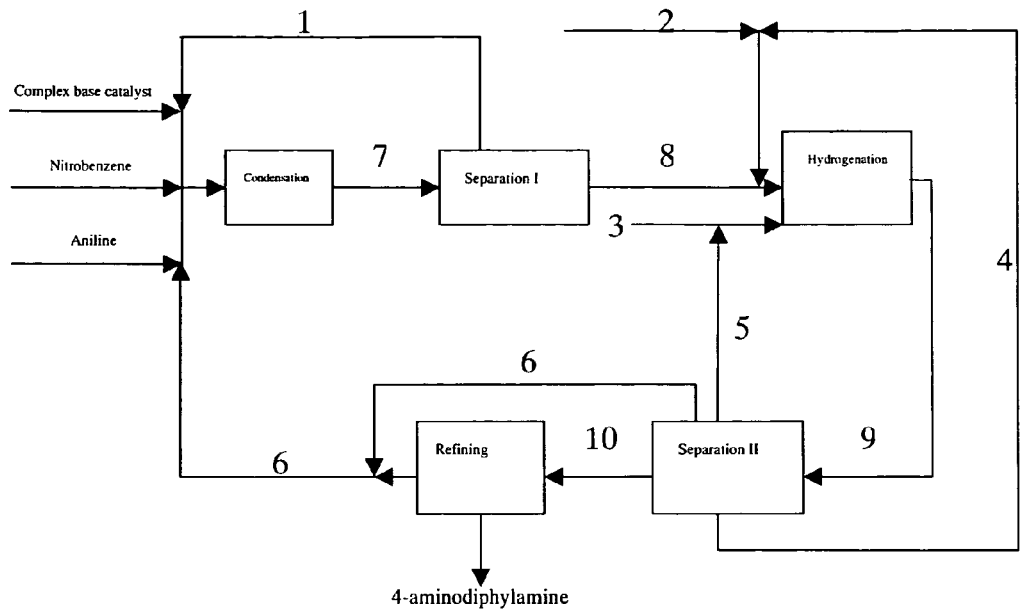

Figure 1. A flow diagram of the process for preparing 4-aminodiphylamine

1 - reused complex base catalyst

2 - powdery composite catalyst

3 - hydrogenation solvent

4 - reused, optionally at least partially regenerated, powdery composite catalyst 5 - reused hydrogenation solvent 6 - reused aniline 7 - condensation liquid 8 - separation I liquid (i.e., condensation liquid from which the complex base catalyst has been separated)

9 - hydrogenation liquid

10 - crude product of 4-aminodiphylamine

PROCESS FOR PREPARING 4-AMINODIPHENYLAMINE

CROSS REFERENCE OF RELATED APPLICATIONS

The present application claims priority to CN03148566.9, CN03148195.7, CN03148194.9, CN03148191.4, CN03148565.0, CN03148200.7, CN03148198.1, CN03148196.5, filed on Jul. 4, 2003, which are incorporated herein by reference in their entirety and for all purposes.

TECHNICAL FIELD

The present invention relates to a process for preparing 4-aminodiphenylamine. In particular, the present invention relates to a continuous process for preparing 4-aminodiphenylamine, which process uses nitrobenzene and aniline as raw materials, a complex base catalyst as condensation catalyst and a conventional hydrogenation catalyst or a powdery composite catalyst as hydrogenation catalyst, and comprises five process stages: condensation; separating, recovering and reusing the complex base catalyst; hydrogenation; separating, recovering and reusing aniline and optionally separating, recovering and reusing hydrogenation solvent, and if necessary, separating, recovering and reusing the hydrogenation catalyst which is optionally at least partially regenerated; and refining.

BACKGROUND OF THE INVENTION

4-Aminodiphenylamine is an important intermediate of antioxidant and stabilizer, and is an important chemical product for rubber industry and polymer industry. Depending on starting materials, current methods for preparing 4-aminodiphenylamine include: (1) aniline method, wherein p-nitro-chlorobenzene and aniline as raw materials react in the presence of a catalyst to produce 4-nitrodiphenylamine, then 4-nitrodiphenylamine is reduced by sodium sulfide to form 4-aminodiphenylamine; (2) formanilide method, wherein formic acid and aniline are used as starting materials to prepare formanilide, which in turn reacts with p-nitro-chlorobenzene in the presence of an acid-binding agent such as potassium carbonate, to produce 4-nitrodiphenylamine, and then 4-nitrodiphenylamine is reduced by sodium sulfide to form 4-aminodiphenylamine; (3) diphenylamine method, wherein diphenylamine as raw material is nitrosated using a nitrite in an organic solvent to produce N-nitrosodiphenyamine, which rearranges to 4-nitrosodiphenyamine hydrochloride under the action of anhydrous hydrogen chloride, then 4-nitrosodiphenyamine hydrochloride is neutralized with a base to give 4-nitrosodiphenyamine, and said 4-nitrosodiphenyamine is finally reduced to 4-aminodiphenylamine by sodium sulfide. Although these methods use different starting materials, traditional sodium sulfide is used as reducing agent to prepare 4-aminodiphenylamine. These reactions suffer from severe reaction conditions, complex operation, higher energy consumption, lower yield, higher cost and environment pollution caused by concomitant waste water, waste gas and waste residue.

Among the preparation methods of 4-aminodiphenylamine, one utilizes nitrobenzene or nitrobenzene and aniline or nitrosobenzene as raw materials to carry out condensation reaction, and then utilizes hydrogen gas to perform hydrogenation to produce 4-aminodiphenylamine. In fact, it was reported in 1901 (Wohl, Chemische Berichte, 34, p. 2442 (1901)) and in 1903 (Wohl, Chemische Berichte, 36, p. 4135 (1903)) that nitrobenzene reacted with aniline under the action of a base to form 4-nitrosodiphenylamine and 4-nitrodiphenylamine. However, said method is neither attached importance to nor developed because of its relatively low yield until 1990s when it is researched and developed again and achieved some progresses (see DE19734055.5, DE19810929.6, and DE19709124.5). The disclosed methods share the following disadvantages: 1) catalysts used are expensive so as to result in excessive high production cost when said catalysts are used in industrial scale production, so that said methods have no advantage in comparison with the current production techniques. For example, tetraalkyl ammonium hydroxide and fluoride used in condensation reaction and noble metal, such as palladium, platinum, rhodium, and the like, used in hydrogenation reaction are expensive. The instability of tetraalkyl ammonium hydroxide imparts some difficulty to recovery and reuse of tetraalkyl ammonium hydroxide. The use of noble metal hydrogenation catalysts applies higher requirements to raw materials and equipments; 2) the yield is relatively low, and only suitable for laboratory research. This is an important reason why said methods are very difficult to be industrialized; 3) operation is complicated, and this isn't in favor of continuous operation and limits the production scale; 4) separation is difficult and purity of product is not high.

U.S. Pat. No. 6,395,933 discloses a process for synthesizing 4-aminodiphenylamine by reacting nitrobenzene and a substituted aniline at a certain temperature in the presence of a strong base and a phase-transfer catalyst. The process is unsatisfactory in yield and there are many side reactions. In the mixture of 4-nitrodiphenylamine and 4-nitrosodiphenylamine produced, the proportion of 4-nitrodiphenylamine is too high so that too much hydrogen is consumed during hydrogenation reaction and the production cost is thereby increased. Furthermore, said process needs an oxidizing agent so that it is not suitable for industrial production.

WO9300324 discloses a process for preparing 4-aminodiphenylamine by reacting nitrobenzene and aniline at a proper temperature in a proper solvent in the presence of a base with the content of proton materials in solution being controlled. Said process requires a solvent and has to control the content of proton materials in solution. The introduction of the solvent results in the increment of energy consumption and separation difficulty. Controlling the content of proton materials gives rise to difficulty of operating and controlling the reaction. In particular, at the later stage of condensation reaction, controlling the content of proton materials in the solution, which mainly means dehydrating to a lower water content, will prolong reaction time and partial aniline will be entrained out. The later stage, the more difficult removing the proton materials. Controlling the proton materials at a certain level is difficult, and goes against industrial production. The expensive tetraalkyl quaternary amine base catalyst will quickly decompose in the course of controlling the content of proton materials to a range of from 0.5 to 4 percent, resulting in the increment of the production cost.

SUMMARY OF THE INVENTION

The invention aims at the selection of inexpensive catalysts with good performance used for condensation and hydrogenation reactions and at the selection of a process suitable for industrial scale production, to continuously produce 4-aminodiphenylamine.

The present invention utilizes a complex base catalyst as condensation catalyst and a conventional hydrogenation catalyst or a powdery composite catalyst as hydrogenation catalyst, to prepare 4-aminodiphenylamine in a continuous process comprising five process stages of condensation; separation I (separating, recovering and reusing the complex base catalyst); hydrogenation; separation II (separating, recovering and reusing aniline, optionally separating, recovering and reusing hydrogenation solvent, and if necessary, separating, recovering and reusing hydrogenation catalyst which is optionally at least partially regenerated); and refining.

BRIEF DESCRIPTION OF THE FIGURE

FIG. 1 is a flowchart showing an embodiment of the process for preparing 4-aminodiphenylamine according to the present invention.

DETAILED DESCRIPTION OF THE INVENTION

According to an embodiment of the present invention, a process for preparing 4-aminodiphenylamine is provided, which process comprises five process stages: condensation; separation I, i.e. separating, recovering and reusing complex base catalyst; hydrogenation; separation II, i.e. separating, recovering and reusing aniline and optionally separating, recovering and reusing hydrogenation solvent, and if necessary, separating, recovering and reusing the hydrogenation catalyst which is optionally at least partially regenerated; and refining, and uses nitrobenzene and aniline as raw materials and a complex base catalyst as condensation catalyst.

In another embodiment according to the present invention, hydrogenation catalyst used in the hydrogenation reaction is selected from the group consisting of conventional hydrogenation catalysts comprising Group VIII element(s) of the Periodic Table or Cu, Cr, Zn or Mn as active component and/or co-catalyst component or powdery composite catalysts.

In still another embodiment according to the present invention, the powdery composite catalyst comprises nickel, aluminum and component A, said component A being at least one selected from the group consisting of Fe, Cu, Co, Mn, Cr, Mo, B and P, and wherein the content of nickel ranges from 25 to 99.9 wt.-%, and the total content of aluminum and component A ranges from 0.1 to 75 wt.-%.

In still another embodiment according to the present invention, the condensation reaction is carried out under conditions of a molar ratio of nitrobenzene to aniline of from 1:1 to 1:15, a reaction temperature of from 20 to 150° C., a reaction pressure of from 0.005 to 0.1 MPa (absolute pressure) and a reaction time of from 3.5 to 6 h.

In still another embodiment according to the present invention, in separation I, the complex base catalyst is recovered by neutralizing the reaction system with an acidic matter to conduct separation, then basifying aqueous phase using a base, wherein said acidic matter is selected from the group consisting of inorganic acids, combinations of oxides thereof and water, and inorganic acid-form salts, preferably hydrochloric acid, sulfuric acid, nitric acid, carbonic acid, sodium bicarbonate, a combination of carbon dioxide and water, a combination of sulfur trioxide and water; said base is selected from the group consisting of hydroxides or oxides of alkali metals and alkaline earth metals, and the acidic matter and the base are chosen according to type of tetraalkyl ammonium salt and base in the complex base catalyst.

In still another embodiment according to the present invention, molar ratio of hydroxide ion in the complex base catalyst to nitrobenzene is in a range of from 1:4 to 4:1.

In still another embodiment according to the present invention, the complex base catalyst used in the condensation reaction comprises a tetraalkyl ammonium hydroxide, an alkali metal hydroxide, and a tetraalkyl ammonium salt.

In still another embodiment according to the present invention, molar ratio of tetraalkyl ammonium hydroxide to alkali metal hydroxide to tetraalkyl ammonium salt in the complex base catalyst equals (0–9):(0.5–3):(0.5–3), and the sum of concentration of tetraalkyl ammonium hydroxide, alkali metal hydroxide and tetraalkyl ammonium salt ranges from 10 to 100 percent by weight.

In still another embodiment according to the present invention, the used complex base catalyst is prepared as follows: tetraalkyl ammonium hydroxide, alkali metal hydroxide or oxide and tetraalkyl ammonium salt, at desired molar ratio, are stirred in water at a temperature of from 0 to 90° C. until being homogeneous, to form an aqueous form of the complex base catalysts, said tetraalkyl ammonium hydroxide, alkali metal hydroxide or oxide and tetraalkyl ammonium salt as raw materials being in solid form or in aqueous solution form.

In still another embodiment according to the present invention, the used complex base catalyst is prepared as follows: tetraalkyl ammonium hydroxide, alkali metal hydroxide or oxide and tetraalkyl ammonium salt, at desired molar ratio, are stirred in water at a temperature of from 0 to 90° C. until being homogeneous, then water is completely removed through azeotropic process by adding benzene, to form an anhydrous form of the complex base catalysts, said tetraalkyl ammonium hydroxide, alkali metal hydroxide or oxide and tetraalkyl ammonium salt as raw materials being in solid form or in aqueous solution form.

In still another embodiment according to the present invention, the tetraalkyl ammonium salt is represented by a general formula of

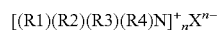

$$[(R1)(R2)(R3)(R4)N]^+_n X^{n-}$$

wherein R1, R2, R3 and R4, which may be identical or different, can be alkyl having from 1 to 4 carbon atoms, said alkyl being optionally substituted by a hydrophilic substituent; $X^{n-}$ is selected from the group consisting of halide ion, sulfate radical, carbonate radical, phosphate radical, bicarbonate radical, bisulfate radical, $C_1$–$C_2$-alkyl carbonate radical, $C_1$–$C_2$-alkyl sulfate radical, etc.; and n is a value of from 1 to 2.

In still another embodiment according to the present invention, in said general formula of the tetraalkyl ammonium salt, at least one of R1, R2, R3 and R4 is substituted by a hydrophilic substituent selected from the group consisting of hydroxy, methoxy, polyether, cationic polyamide, polyester, polyethylene polyamine and highly water-soluble quaternary ammonium salt-containing radical.

In still another embodiment according to the present invention, the tetraalkyl ammonium salt is a hydrophilic substituent-carring tetraalkyl ammonium salt selected from the group consisting of poly-methylated triethylene tetraamine sulfate, poly-methylated diethylene triamine carbonate, N,N-dimethyl-N,N-bis(methoxyethyl) ammonium carbonate, N-methyl-N,N,N-tri(methoxyethyl) ammonium carbonate, N,N,N-trimethyl-N-hydroxyethyl ammonium carbonate, trimethyl hydroxyethyl ammonium chloride, N,N,N-trimethyl-N-ethoxylated (1–4 moles of ethylene oxide) ethyl ammonium carbonate, N,N,N-trimethyl-N-ethoxylated (1–4 moles of ethylene oxide) propyl ammonium carbonate, N,N,N-trimethyl-N-ethoxylated (1–4 moles of ethylene oxide) propyl ammonium chloride, N,N-dimethyl-N,N-bis(ethoxylated (1–4 moles of ethylene oxide) propyl) ammonium carbonate.

In still another embodiment according to the present invention, the tetraalkyl ammonium salt is selected from the group consisting of tetramethyl ammonium carbonate, tetramethyl ammonium methyl-carbonate, tetraethyl ammonium carbonate, tetraethyl ammonium ethyl-carbonate, tetramethyl ammonium sulfate, tetramethyl ammonium methyl-sulfate, tetraethyl ammonium sulfate, and tetraethyl ammonium ethyl-sulfate.

In still another embodiment according to the present invention, the tetraalkyl ammonium salt is those prepared by reacting trialkyl amine with $di(C_1-C_2)$alkyl carbonate or $di(C_1-C_2)$alkyl sulfate in polar solvent.

In still another embodiment according to the present invention, the reaction for the preparation of the tetraalkyl ammonium salt is carried out under the following conditions: reaction pressure ranges from 0.1 to 3.0 MPa, reaction temperature ranges from 50–200° C., reaction time ranges from 1.5 to 6 h, molar ratio of trialkyl amine to $di(C_1-C_2)$ alkyl carbonate or $di(C_1-C_2)$alkyl sulfate ranges from 2:1 to 1:2, the polar solvent used is methanol, ethanol or isopropanol, and the polar solvent is used in an amount of from 1 to 10 times of weight of the trialkyl amine.

In still another embodiment according to the present invention, the condensation reaction is carried out in the absence of oxygen.

In still another embodiment according to the present invention, it is not necessary to add additionally or control proton materials during the condensation reaction.

In still another embodiment according to the present invention, the condensation reaction is carried out without a solvent.

In still another embodiment according to the present invention, an amount of complex base catalyst is added during initial stage of the condensation reaction and only tetraalkyl ammonium salt component and/or alkali metal hydroxide or oxide component of the complex base catalyst are replenished in the course of the reaction.

In still another embodiment according to the present invention, the condensation process stage is conducted in a circulating system consisting of a condensing circulating pump, a falling film reactor and a first reactor, and optional subsequent reactor(s).

In still another embodiment according to the present invention, a falling film reactor is used in the condensation process stage and the falling film reactor utilizes ethanol vapor, hot water, steam or methanol vapor as heat medium.

In still another embodiment according to the present invention, the hydrogenation reaction is carried out under the following conditions: hydrogen gas is used as reducing agent; volume ratio of gas to liquid is in a range of from 10:1 to 1500:1, weight ratio of solid to liquid is in a range of from 0.5:100 to 16:100 when non-fixed bed hydrogenation process is used, and weight ratio of solvent to separation I liquid (i.e., condensation liquid from which the complex base catalyst has been separated) is in a range of from 1:10 to 5:10, with the gas representing hydrogen gas, the liquid including solvent and separation I liquid, and the solid representing hydrogenation catalyst; the temperature of hydrogenation reaction ranges from 50 to 150° C., the pressure of the reactor ranges from 0.2 to 6.0 MPa (absolute pressure), and the reaction time ranges from 2 to 7 h.

In still another embodiment according to the present invention, the powdery composite catalyst used in the hydrogenation reaction is prepared by mixing powdery nickel, powdery aluminum and component A in desired proportion, then melting them at high temperature, followed by pulverizing them into powder after discharging and quenching, and then treating the powder with an aqueous solution of a hydroxide.

In still another embodiment according to the present invention, a magnetic separator is used to recover magnetic powdery composite catalyst after the hydrogenation reaction.

In still another embodiment according to the present invention, recovered powdery composite catalyst is conveyed back to the hydrogenation reactor via a Venturi type mixed solid-liquid conveying equipment utilizing feeding power.

In still another embodiment according to the present invention, deactivated powdery composite catalyst is regenerated by treating with ultrasonic vibration and/or strong base.

In still another embodiment according to the present invention, the solvent used in the hydrogenation reaction is an alcohol and/or water.

In still another embodiment according to the present invention, the refining is performed through three-column continuous rectification plus batch rectification process, and wherein rectification column 1, rectification column 2 and rectification column 3 are operated at a vacuum degree ranging independently from 0.09 to 0.098 MPa; a still temperature of from 260 to 290° C., from 260 to 300° C. and from 120 to 170° C., respectively; a reflux ratio of from 2:1 to 10:1, from 1:0.5 to 1:4 and from 1:0.5 to 1:2, respectively; and the batch rectification column is operated at a vacuum degree of from 0.09 to 0.098 MPa, and a still temperature of from 280 to 330° C.

In the process according to the present invention, "separation I" means separating, recovering and reusing complex base catalyst; and "separation II" means separating, recovering and reusing aniline and optionally separating, recovering and reusing hydrogenation solvent, and if necessary, separating, recovering and reusing hydrogenation catalyst which is optionally at least partially regenerated. The expression "optionally separating, recovering and reusing hydrogenation solvent" as used herein intends to means that, when water is used as hydrogenation solvent, the water is optionally recovered and reused, and when an alcohol solvent, which will be described hereinbelow, is used as hydrogenation solvent, the alcohol hydrogenation solvent is separated, recovered and reused.

With reference to the FIG. 1, in a preferred embodiment according to the present invention, the process for preparing 4-aminodiphenylamine according to the present invention comprises the steps of:

continuously feeding nitrobenzene, aniline and a complex base catalyst, at desired proportion, to condensation process stage via metering pumps, and allowing them to react to form a condensation liquid (7) containing 4-nitrodiphenylamine, 4-nitrosodiphenylamine and/or salts thereof;

continuously feeding the condensation liquid (7) to separation I process stage, where the complex base catalyst is recovered by neutralizing the condensation liquid (7) with an acidic matter to conduct separation, then basifying aqueous phase using a base, and then the recovered complex base catalyst (1) is recycled back to the condensation process stage;

continuously feeding separation I liquid (i.e., the condensation liquid from which the complex base catalyst has been separated) (8), hydrogenation solvent, including supplementary hydrogenation solvent (3) and optionally recovered hydrogenation solvent (5), at desired proportion to hydrogenation process stage, and allowing them to react with hydrogen gas under the catalytic action of a powdery composite catalyst, including supplementary powdery composite catalyst (2) and reused, optionally at least partially regenerated, powdery composite catalyst (4), to form a hydrogenation liquid (9) containing 4-aminodiphenylamine;

feeding the hydrogenation liquid (9) to separation II process stage, where (a) powdery composite catalyst (4), which is to be recycled back to the hydrogenation process stage directly or after being at least partially regenerated, (b) aniline (6), which is to be recycled back to the condensation process stage, and (c) optionally, hydrogenation solvent (5), which is to be recycled back to the hydrogenation process stage, are obtained; and feeding crude 4-aminodiphenylamine (10), from which most of aniline has been separated, to refining process stage, where (a) partial aniline (6), which is to be recycled back to the condensation process stage, and (b) the finished 4-aminodiphenylamine are obtained. The whole process is conducted continuously.

In the condensation reaction, molar ratio of nitrobenzene to aniline is in a range of from 1:1 to 1:15; reaction temperature may be in a range of from 20 to 150° C., preferably from 50 to 90° C., and controlling the reaction temperature not higher than 90° C. can result in a decomposition ratio of the complex base catalyst of less than 0.5 percent during the condensation; reaction pressure may vary from 0.005 to 0.1 MPa (absolute pressure); and residence time of the stuff in the whole condensation reaction system is in a range of from 3.5 to 6 h.

The complex base catalyst used in the condensation reaction comprises a tetraalkyl ammonium hydroxide, an alkali metal hydroxide, a tetraalkyl ammonium salt and optional water, wherein the concentration sum of tetraalkyl ammonium hydroxide, alkali metal hydroxide and tetraalkyl ammonium salt is in a range of from 10 to 100 percent by weight, preferably from 25 to 38 percent by weight, and wherein the molar ratio of tetraalkyl ammonium hydroxide to alkali metal hydroxide to tetraalkyl ammonium salt is (0–9):(0.5–3):(0.5–3). The combination of part tetraalkyl ammonium hydroxide and inexpensive alkali metal hydroxide or oxide and tetraalkyl ammonium salt can attain the same object as attained in the prior art where highly pure tetraalkyl ammonium hydroxide is used as catalyst. In the condensation reaction mixture, the molar ratio of hydroxide ion in complex base catalyst to nitrobenzene is in a range of from 1:4 to 4:1.

The complex base catalysts used for the condensation reaction is prepared as follows: tetraalkyl ammonium hydroxide, alkali metal hydroxide or oxide and tetraalkyl ammonium salt, at a molar ratio of (0–9):(0.5–3):(0.5–3), are stirred in water at a temperature of from 0 to 90° C. until being homogeneous, to form an aqueous form of the complex base catalysts. Then water can be completely removed by adding benzene through azeotropic process, to form an anhydrous form of the complex base catalysts. Said tetraalkyl ammonium hydroxide, alkali metal hydroxide or oxide and tetraalkyl ammonium salt as raw materials can be in solid form or in aqueous solution form.

In the course of industrial production, the reaction mixture unavoidably contacts with carbon dioxide and carbon monoxide in ambient air and hydrogen, so that the tetraalkyl ammonium hydroxide will decrease in amount by converting to tetraalkyl ammonium carbonate. In the case where only a tetraalkyl ammonium hydroxide is used as catalyst, the transformation of tetraalkyl ammonium hydroxide into ammonium salt will decrease the quantity of the catalyst, so that there need supply the catalyst and get rid of the ammonium salt. In contrast, with the complex base catalyst according to the present invention, there needs no any complex technology but increasing the content of alkali metal hydroxide or oxide in the complex base catalyst.

According to the present invention, nitrobenzene and aniline are condensed to form 4-nitrodiphenylamine and 4-nitrosodiphenylamine and/or their salts at certain conditions using the complex base catalyst. Anhydrous form of the complex base catalyst may be used to convert nitrobenzene and aniline to 4-nitrodiphenylamine and 4-nitrosodiphenylamine and/or their salts in the condensation reaction according to the present invention. The selectivity and conversion of the reaction attain to the desired level at an anhydrous condition.

In the case of using a complex base catalyst, it is possible not to severely control proton materials such as water, methanol and the like, thereby avoiding as much as possible the loss of the complex base catalyst and operation complexity caused by the control of proton materials. Without limited to any specific theory, it is believed that the integrated action of tetraalkyl ammonium hydroxide, alkali hydroxide and tetraalkyl ammonium salt in the complex base catalyst gives rise to such a result, thereby reducing the difficulty of operating and controlling the reaction. It is believed that the use of the complex base catalyst comprising tetraalkyl ammonium hydroxide, alkali hydroxide and tetraalkyl ammonium salt makes the control of proton materials, for example, water in reaction system unimportant. That is to say, condensation reaction can be carried out with the conversion and selectivity being not affected no matter whether there are no proton materials such as water in the solution or there is a high content of proton materials such as water in the solution. Thus, the difficulty of operating and controlling the reaction can be reduced and the quantity of aniline entrained out by azeotropic dehydration can be decreased, so that the process is more suitable for industrial scale production.

In the process according to the present invention, proton materials such as water no longer construct a restricting factor of the reaction, and the selectivity and conversion can attain to the desired level whether or not there are proton materials such as water. Furthermore, it has been found that the decomposition rate of the complex base catalyst is lower than that of the single tetraalkyl ammonium hydroxide.

In a preferred embodiment of the present invention, condensation reaction can be carried out as follows: nitrobenzene, aniline and complex base catalyst, at desired proportion, are continuously fed via metering pumps to a falling film reactor to be heated and allowed to condense; the condensation liquid in the falling film reactor is discharged from the bottom of the reactor into a first reactor to continue condensation reaction; a part of the condensation liquid from the bottom of the first reactor is conveyed back to the falling film reactor via a circulating pump, to establish a local circulating system of the condensation reaction according to the present invention. The circulating system mainly consists of the falling film reactor and the first reactor, and reactants continuously circulate in said circulating system via the condensation circulating pump. The circulating process maintains an amount of condensation liquid sufficient to form a uniform film in the falling film reactor. The falling film reactor may utilize ethanol vapor, hot water, steam or methanol vapor, preferably ethanol vapor as heat medium, to make the temperature of the system very homogeneous and avoid local overheating. That there is hardly back-mixing of reaction liquid in a falling film reactor significantly decreases the contact chance of product and raw materials and minimizes the side reaction. The local circulating system including the falling film reactor enhances the condensation reaction rate and reduces the reaction time, which is shortened from more than ten hours to 3.5–6 hours.

It has also been found that continuous film reaction is higher than complete mixing reaction in both selectivity and yield. During this reaction, nitrobenzene reacts with aniline to form 4-nitrosodiphenylamine; nitrobenzene can also react with 4-nitrosodiphenylamine to form 4-nitrodiphenylamine, and nitrobenzene itself is reduced to nitrosobenzene, which in turn can react with aniline to form azobenzene. The latter reaction goes against main reaction and reduces the selectivity of the reaction. At the beginning of reaction, the quantity of nitrobenzene is relatively bigger. Nitrobenzene is gradually converted to 4-nitrosodiphenylamine and the quantity of nitrobenzene becomes smaller along with the reaction. The use of the continuous film reactor reduces the contact and reaction between nitrobenzene added and 4-nitrosodiphenylamine which is later formed (when the reactants enter the reactor to react, the concentration of nitrobenzene is relatively higher yet the concentration of 4-nitrosodiphenylamine is relatively lower, while at the end of the reaction, the concentration of 4-nitrosodiphenylamine is relatively higher yet the concentration of nitrobenzene is relatively lower), that is, the opportunity that nitrobenzene is reduced to nitrosobenzene by 4-nitrosodiphenylamine, thereby reducing reaction between nitrobenzene and aniline to form azobenzene.

In the condensation reaction of nitrobenzene and aniline in the presence of the complex base catalyst, the main side reaction is to form by-products, azobenzene and phenazine. It has been found that the bigger the quantity of aniline, the less the side reaction to convert nitrobenzene to phenazine. Another by-product in the reaction is azobenzene. Azobenzene can be easily transformed into aniline at the hydrogenation process stage, so that it can be reused in the production. Therefore, the molar ratio of nitrobenzene to aniline employed in the invention is selected as from 1:1 to 1:15.

Furthermore, in the process according to the present invention, condensation reaction can be performed under proper ratio of nitrobenzene and aniline without the introduction of any solvent into the system and a good yield can be achieved.

The invention improves the yield of the condensation reaction and makes the reaction moving towards desired direction utilizing the above method.

Those skilled in the art can contemplate that the condensation reaction according to the present process might employ more stages of reactors in series.

In the condensation process stage, it is unavoidable to lose part of complex base catalyst used in condensation process along with the reaction. It is possible to supply only alkali metal hydroxide component and tetraalkyl ammonium salt component of the complex base catalyst when replenishing the catalyst, and their molar ratio is in a range of from 4:1 to 1:4. Alkali metal oxide can be used to replace alkali metal hydroxide, and its amount can be gotten by conversion from corresponding hydroxide.

The tetraalkyl ammonium salts useful in the present invention can be represented by a general formula of $$[(R1)(R2)(R3)(R4)N]^+_n X^{n-}$$

wherein R1, R2, R3 and R4, which may be identical or different, can be alkyl having from 1 to 4 carbon atoms, said alkyl can carry a hydrophilic substituent selected from the group consisting of hydroxy, methoxy, polyether, cationic polyamide, polyester, polyethylene polyamine, highly water-soluble quaternary ammonium salt-containing radical, etc., $X^{n-}$ is selected from the group consisting of halide ions, sulfate radical, carbonate radical, phosphate radical, bicarbonate radical, bisulfate radical, $C_1$–$C_2$-alkyl carbonate radical, $C_1$–$C_2$-alkyl sulfate radical, etc., and n is a value of from 1 to 2. Examples of the tetraalkyl ammonium salts include, but are not limited to, poly-methylated triethylene tetraamine sulfate, poly-methylated diethylene triamine carbonate, N,N-dimethyl-N,N-bis(methoxyethyl) ammonium carbonate, N-methyl-N,N,N-tri(methoxyethyl) ammonium carbonate, N,N,N-trimethyl-N-hydroxyethyl ammonium carbonate, trimethyl hydroxyethyl ammonium chloride, N,N,N-trimethyl-N-ethoxylated (1–4 moles of ethylene oxide) ethyl ammonium carbonate, N,N,N-trimethyl-N-ethoxylated (1–4 moles of ethylene oxide) propyl ammonium carbonate, N,N,N-trimethyl-N-ethoxylated (1–4 moles of ethylene oxide) propyl ammonium chloride, N,N-dimethyl-N,N-bis(ethoxylated (1–4 moles of ethylene oxide) propyl) ammonium carbonate, tetramethyl ammonium carbonate, tetramethyl ammonium methyl-carbonate, tetraethyl ammonium carbonate, tetraethyl ammonium ethyl-carbonate, tetramethyl ammonium sulfate, tetramethyl ammonium methyl-sulfate, tetraethyl ammonium sulfate, and tetraethyl ammonium ethyl-sulfate.

The tetraalkyl ammonium hydroxides used in the complex base catalyst can be represented by a formula of $R'_4N^+OH^-$, wherein $R'$ is independently an alkyl having one or two carbon atoms. The tetraalkyl ammonium hydroxide may be prepared from corresponding tetraalkyl ammonium salt and base in polar solvent according to a process known per se.

The alkali metal hydroxides or oxides include hydroxides and oxides of lithium, sodium, potassium and rubidium, such as sodium hydroxide, potassium hydroxide, lithium hydroxide, sodium oxide or potassium oxide.

The tetraalkyl ammonium alkyl-carbonates or tetraalkyl ammonium alkyl-sulfates useful in the present invention can be prepared by the reaction of trialkyl amine and di($C_1$–$C_2$) alkyl carbonate or di($C_1$–$C_2$)alkyl sulfate in polar solvent.

According to the present invention, in the preparation of tetraalkyl ammonium alkyl-carbonates or tetraalkyl ammonium alkyl-sulfates, the reaction temperature varies from 50 to 200° C., preferably from 60 to 150° C., and reaction pressure varies from 0.1 to 3 MPa (gauge pressure). In general, the pressure depends on the selected temperature, as well as type and amount of the solvent, namely, the less the amount of solvent, the higher the system pressure; and the higher the temperature, the higher the pressure. In the present invention, the reaction pressure is preferably controlled in a range of from 0.4 to 2 MPa to obtain higher product yield.

In the reaction for the preparation of tetraalkyl ammonium alkyl-carbonate or tetraalkyl ammonium alkyl-sulfate according to the present invention, the molar ratio of trialkyl amine to di($C_1$–$C_2$)alkyl carbonate or di($C_1$–$C_2$)alkyl sulfate is chosen as from 2:1 to 1:2. If the proportion of trialkyl amine is too high, then trialkyl amine will be superabundant in the reaction system and thus impose operational difficulty to subsequent processes and pollutes the environment. If the proportion of trialkyl amine is too low, then di($C_1$–$C_2$)alkyl carbonate or di($C_1$–$C_2$)alkyl sulfate will be superabundant, resulting in the loss of di($C_1$–$C_2$)alkyl carbonate or di($C_1$–$C_2$)alkyl sulfate in the subsequent reaction, thereby increasing the production cost.

In the process for the preparation of tetraalkyl ammonium alkyl-carbonate or tetraalkyl ammonium alkyl-sulfate according to the present invention, reaction time of trialkyl amine and di($C_1$–$C_2$)alkyl carbonate or di($C_1$–$C_2$)alkyl sulfate is in a range of from 1.5 to 6 h. At the initial stage of the reaction, the reaction rate is high, and exothermic phenomenon is obvious. With consumption of raw materials, the reaction became slow and heat release is gradually reduced. During the reaction, the amount of cooling water is continuously adjusted to keep reaction temperature and pressure in a certain range.

The polar solvents useful in the reaction for the preparation of tetraalkyl ammonium alkyl-carbonate or tetraalkyl ammonium alkyl-sulfate according to the present invention include methanol, ethanol or isopropyl alcohol. The amount of solvents used varies from 1 to 10 times of weight of trialkyl amine.

In separation I process stage, the condensation liquid containing 4-nitrodiphenylamine and 4-nitrosodiphenylamine and/or salts thereof is filtered, and an acidic matter is added to the filtrate to reduce pH of the solution to about 8, then layers are separated. The obtained organic phase is a mixture of 4-nitrodiphenylamine and 4-nitrosodiphenylamine, i.e. separation I liquid. A base is added to the obtained aqueous phase at such an amount that equivalent ratio of the base to above-added acidic matter is in a range of from 1:1 to 3:1, to give the complex base catalyst. If necessary, the recovered complex base catalyst may be concentrated prior to being recycled back to the condensation process stage.

The acidic matters useful in the separation I process stage may be selected from the group consisting of inorganic acids, combinations of oxides thereof and water, and inorganic acid-form salts, for example, hydrochloric acid, sulfuric acid, nitric acid, carbonic acid, sodium bicarbonate, a combination of carbon dioxide and water, a combination of sulfur trioxide and water, and the like; and the base used may be selected from the group consisting of hydroxides or oxides of alkali metals and alkaline earth metals. It is desired to choose suitable acidic matter and base based on the type of the tetraalkyl ammonium salt and the base in the complex base catalyst. The principles for making such a choice are well known by ordinarily skilled persons in the art. For example, if tetraalkyl ammonium salt is a chloride, hydrochloride acid is chosen as the acidic matter in order to avoid to introduce other impurities. For another example, if tetraalkyl ammonium salt is a carbonate, then a combination of carbon dioxide and water can be used to neutralize the filtrate, and calcium hydroxide is used to basify the aqueous phase.

It should be pointed out that the present invention avoids the problem that the complex base catalysts thermally decompose in the hydrogenation reaction by separating the complex base catalysts from 4-nitrodiphenylamine and 4-nitrosodiphenylamine in separation I process stage utilizing an acidic matter, thereby largely enlarging the selectable range of hydrogenation catalyst. The hydrogenation catalysts useful in the hydrogenation reaction according to the present invention may be any conventional hydrogenation catalyst comprising Group VIII element(s) of the Periodic Table or Cu, Cr, Zn, Mn etc. as active component and/or co-catalyst component or a powdery composite catalyst. The temperature of hydrogenation reaction may range from 50 to 150° C., and the hydrogenation reactor may employ one-stage or multi-stage of flow reactor(s), or one-stage or multi-stage of fixed bed reactor(s) in series. If a catalyst in a form suitable for fixed bed reactor, for example, granular catalyst, is used, the process may be adjusted in a manner well known by those skilled in the art, for example, there needs not filter the hydrogenation catalyst in separation II process staged described hereinbelow, and there needs not recover hydrogenation catalyst using a magnetic separator in the hydrogenation process. These embodiments are also encompassed in the present invention.

Now hydrogenation and separation II process stages of the process according to the present invention in which a powdery composite catalyst of the present invention as well as flow reactor hydrogenation process is employed are described.

In the hydrogenation reaction of said embodiment of the present invention, hydrogen gas can be used as reducing agent. The reaction temperature is in a range of from 50 to 150° C., the pressure is in a range of from 0.2 to 6.0 MPa (absolute pressure), and the reaction time varies from 2 to 7 h. Volume ratio of gas to liquid is in a range of from 10:1 to 1500:1, weight ratio of solid to liquid is in a range of from 0.5:100 to 16:100, with the gas representing hydrogen gas, the liquid including hydrogenation solvent and separation I liquid, and the solid representing powdery composite catalyst.

In the practice of the invention, alcohols and/or water can be used as hydrogenation solvent. As alcohols, methanol, ethanol and isopropyl alcohol are preferred. The hydrogenation solvent can be used in such an amount that weight ratio of hydrogenation solvent to separation I liquid is in a range of from 1:10 to 5:10.

The powdery composite catalysts useful in the hydrogenation reaction according to the present invention comprise nickel, aluminum and component A which is at least one selected from the group consisting of Fe, Cu, Co, Mn, Cr, Mo, B and P, wherein the content of nickel is in a range of from 25 to 99.9 wt.-%, and the total content of aluminum and component A is in a range of from 0.1 to 75 wt.-%. The particle size of the catalysts may vary from 40 to 300 mesh.

The modifying agent A, which is at least one selected from the group consisting of Fe, Cu, Co, Mn, Cr, Mo, B and P, can modify the crystalline state of nickel-aluminum alloy so as to achieve the purpose of improving the selectivity of hydrogenation reaction and enhancing the activity of catalyst. The powdery composite catalysts according to the present invention can be prepared by mixing powdery nickel, powdery aluminum and component A at desired proportion, then melting them at high temperature, followed by pulverizing them into powder with a particle size ranging from 40 to 300 mesh after discharging and quenching, and finally, treating the powder with hydroxide aqueous solution. The concentration of hydroxide solution can be in a range of from 5 to 50 weight percent, and the treating temperature is in a range of from 50 to 90° C.

In order to improve the effect of recovering hydrogenation catalysts by magnetic separator in the subsequent process, it is preferred to use at least iron as modifying agent to increase the ferromagnetism of the powdery composite catalysts. Therefore, in a preferred embodiment of the present invention, the powdery composite catalysts according to the present invention can be prepared by taking powdery nickel, powdery aluminum, powdery iron, and optional other modifying agent A, which is selected from the group consisting of Cu, Cr, Co, Mn, Mo, B and P, in desired proportion; melting them into alloy in an induction furnace; ejecting the molten alloy using gas pressure through a nozzle to a copper drum rotating at high speed to quench quickly the alloy with cooling speed being as high as $10^{5-10^6}$ K/sec; pulverizing the cooled alloy using a ball mill into powder with a particle size ranging from 40 to 300 mesh, preferably from 100 to 200 mesh; and finally, treating the powder with 5 to 50 wt.-% aqueous solution of a hydroxide at a temperature of from 50 to 90° C.

According to a preferred embodiment of the invention, hydrogenation reaction can be carried out as follows: separation I liquid, hydrogenation solvent, powdery composite catalyst recovered and, if necessary, complementary fresh powdery composite catalyst are fed to first-stage, second-stage and optional higher-stage hydrogenation reactors via a solid-liquid conveyer, and hydrogen gas is bubbled into the reactors from bottom of the reactors via a hydrogen gas circulator, to carry out the hydrogenation reaction under the above-defined hydrogenation reaction conditions to form crude hydrogenation liquid containing 4-aminodiphenylamine. The powdery composite catalyst entrained out by crude hydrogenation liquid is separated by a settling vessel and a magnetic separator. Solid-liquid phase, which separates from hydrogenation liquid and contains high concentration of the powdery composite catalyst, enters the first-stage reactor to be reused through a mixed solid-liquid conveying device. At the same time, hydrogenation liquid containing 4-aminodiphenylamine is obtained.

The powdery composite catalyst according to the present invention is a solid-state material during the hydrogenation. In industry, a hydrogenation catalyst is typically circulated via a pump, however, when a pump is used to convey a catalyst containing a high concentration of powdery metal, pump cavity is easily damaged and the transportation effect is also not good. The inventors design a Venturi-like solid-liquid conveying device, and circulation of the powdery composite catalyst in hydrogenation system is achieved through a pump-free circulation performed, by skillfully employing the power of the pump for feeding separation I liquid, so that the loss of catalyst is significantly reduced, and the concentration of catalyst in hydrogenation reaction mixture is significantly enhanced.

According to a preferred embodiment, in continuous hydrogenation process, the powdery composite catalyst in crude hydrogenation liquid is recovered through sedimentation and magnetic separator and recycled via a Venturi type solid-liquid conveying device, and circulating hydrogen gas is bubbled into the reactors. The whole hydrogenation step is conducted in a complete mixing flow mode by continuously feeding stock into multistage reactors in series. The hydrogenation solvents can be the recovered and reused.

The hydrogenation liquid having part of the powdery composite catalyst recovered through sedimentation and magnetic separator enters separation II process stage, where the residual powdery composite catalyst in the hydrogenation liquid is recovered from hydrogenation liquid by filtration, and circulated back to the hydrogenation process stage directly or after being at least partially regenerated.

In the hydrogenation reaction according to the present invention, with optionally continuously renewing a minor amount of hydrogenation catalyst, the catalyst concentration in the reaction system can always maintain at a higher level. Such a method of recycling catalyst can always and stably maintain the total activity of catalyst in the system at a higher level and avoid the problem that catalyst activity gradually decreases suffered by the processes employing a fixed bed catalyst. The use of magnetic separator facilitates the recovery of the catalyst, and the designing and application of mixed solid-liquid conveying device make powdery composite catalyst circulating in the hydrogenation system.

In the present invention, deactivation of catalyst usually attributes to that inorganic matter or organic carbon deposition clog pores of the catalyst, so that the active sites of the catalyst are covered, and thereby the activity of the catalyst decreases. Therefore, the present invention employs washing with a high concentration base solution, for example, 5–50 wt.-% aqueous solution of alkali metal hydroxide in combination with ultrasonic vibration to regenerate the catalyst. Ultrasonic vibration facilitates to get rid of the inorganic deposition or organic carbon deposition, while the high concentration base solution can dissolve the aluminum, which isn't dissolved in the first base dissolution, in the catalyst to form new loose pore structures, thereby increasing the activity of the catalyst.

The inventors utilize sedimentation and magnetic separator to recover magnetic hydrogenation catalyst, and design a Venturi type mixed solid-liquid conveying device to convey the catalyst back to hydrogenation reactor using the power of feeding the stocks, thereby achieving the circulation of powdery composite catalyst. The inventors also take out the catalyst after filtration to regenerate it to restore its initial activity. By the two measures, the consumption of catalyst is significantly reduced, and the activity and lifetime of catalyst are improved.

In the separation II process stage, if the hydrogenation solvent used in the hydrogenation reaction is water, after filtering to recover the residual powdery composite catalyst, the layers of the hydrogenation liquid is separated, and the organic phase is continuously fed to aniline column, where aniline is obtained from the column top and recycled back to the condensation process stage, and crude 4-aminodiphenylamine is obtained from column bottom. If the hydrogenation solvent used in the hydrogenation reaction is a mixture of water and an alcohol, after filtering to recover the residual powdery composite catalyst, the layers of the hydrogenation liquid is separated, and aqueous phase and organic phase are respectively rectified to give the alcohol solvent and aniline, which are reused. If the hydrogenation solvent used in the hydrogenation reaction is an alcohol, after filtering to recover the residual powdery composite catalyst, the hydrogenation liquid is fed to a rectification column where the hydrogenation solvent is recovered from the column top and recycled back to the hydrogenation process, and the bottoms is fed to aniline column, where aniline is obtained from the column top and recycled back to the condensation process stage, and crude 4-aminodiphenylamine is obtained from column bottom. The aniline column can be operated at a pressure of from 0.005 to 0.1 MPa (absolute pressure), column bottom temperature is in a range of from 120 to 320° C., and the temperature of gas phase is in a range of from 60 to is 190° C.

The organic phase having most aniline separated in separation II process stage contains 4-aminodiphenylamine, aniline, azobenzene and phenazine, etc. In an embodiment of the present invention, the refining process is conducted through three-column continuous rectification plus batch rectification, wherein the organic phase to be refined is conveyed via a pump into rectification column 1, where aniline, azobenzene and phenazine are taken out from the column top, and crude 4-aminodiphenylamine is discharged from the column bottom. The effluent from the top of rectification column 1 enters rectification column 3, where aniline with a purity of about 99% is distilled from the top of rectification column 3 and can be directly recycled back to condensation process, and azobenzene and phenazine are left in the column bottom. Bottoms of rectification column 1 are conveyed via a pump to rectification column 2, where the finished 4-aminodiphenylamine is distilled from the top of rectification column 2, and bottoms of rectification column 2, after accumulating to a certain amount, are conveyed to batch still, where a minor amount of 4-aminodiphenylamine left in the bottoms is distilled off and conveyed back to rectification column 2, and the other residues are discharged from the still bottom.

In the above refining process according to the present invention, the rectification column 1 is operated at a vacuum degree of from 0.09 to 0.098 MPa, a reflux ratio of from 2:1 to 10:1, a column top temperature of from 80 to 130° C., and a still temperature of from 260 to 290° C.; the rectification column 2 is operated at a vacuum degree of from 0.09 to 0.098 MPa, a reflux ratio of from 1:0.5 to 1:4, a column top temperature of from 140 to 190° C., and a still temperature of from 260 to 300° C.; the rectification column 3 is operated at a vacuum degree of from 0.09 to 0.098 MPa, a reflux ratio of from 1:0.5 to 1:2, a column top temperature of from 80 to 120° C., and a still temperature of from 120 to 170° C.; and the batch rectification column is operated at a vacuum degree of from 0.09 to 0.098 MPa, a column top temperature of from 235–250° C., and a still temperature of from 280 to 330° C. The still temperature of the rectification column 2 is relatively lower, thus coking of 4-aminodiphenylamine can be reduced, and 96% or more of 4-aminodiphenylamine can be distilled off at the top of rectification column 2 operated at a relatively lower still temperature, so that the amount of 4-aminodiphenylamine in the bottoms to be subjected to batch distillation is significantly reduced.

The process for preparing 4-aminodiphenylamine according to the present invention uses nitrobenzene and aniline as raw materials, is continuously conducted in five process stages: condensation; separating the complex base catalyst; hydrogenation; separating aniline, hydrogenation solvent and the hydrogenation catalyst; and refining, and thus is suitable for industrial scale production. The use of the complex base catalysts in condensation process significantly decreases the difficulty of operating and controlling the reaction and renders the water in the reaction system being no longer a reaction-confining factor. The decomposition of complex base catalyst is much less than that of the single tetraalkyl ammonium hydroxide catalyst. The selection of a falling film reactor and raw material proportion improves selectivity of the reaction. There needs no solvent. Selecting a complex base catalyst to catalyze the condensation reaction and separating it prior to the hydrogenation avoid the problem that the complex base catalysts thermally decompose in the hydrogenation reaction, largely enlarge the selectable range of hydrogenation catalysts so that it is possible to select cheaper hydrogenation catalyst to reduce cost, enlarge the temperature range suitable for hydrogenation reaction, make it possible to employ a fixed bed reactor filled with granular catalyst thereby reducing industrial technique difficulty of the hydrogenation reaction, and omitting the extraction step (separating the complex base catalyst from the organic phase using extractant and co-extractant) after hydrogenation. In the case where a powdery composite catalyst is used as hydrogenation catalyst, the hydrogenation catalyst is good at antitoxic performance, by-product is little, conversion and selectivity is high, a magnetic separator can be used to recover magnetic powdery composite catalyst during hydrogenation process; the hydrogenation catalyst is conveyed back to hydrogenation reactor via a Venturi type mixed solid-liquid conveying device using the power of feeding stocks; and catalyst can be regenerated by chemical and/or physical methods, and thus the consumption of catalyst is reduced. In the whole process, reaction conditions is mild, by-product is little, conversion and selectivity is high, the operational strength is low, no corrosive liquid is produced, and environment pollution is reduced. The purity of 4-aminodiphenylamine can exceed 99 wt.-%, and the yield in the whole industrial production process can be over 95%.

EXAMPLES

The following examples further describe the invention, but do not make limitation to the invention in any way.

Example 1

Preparation of a Complex Base Catalyst

To a 1000 ml three-necked flask equipped with a condenser and a stirrer were added 227.5 g of 20 wt.-% aqueous solution of tetramethyl ammonium hydroxide (0.5 mol), 10 g (0.25 mol) of sodium hydroxide and 346 g of 30 wt.-% aqueous solution of tetramethyl ammonium carbonate (0.5 mol). The mixture was homogeneously stirred at 72–77° C. to give a complex base catalyst having a concentration of 27.3 wt.-%.

Example 2

Preparation of a Powdery Composite Catalyst 46 g of powdery nickel, 51 g of powdery aluminum, and 3 g of powdery iron were taken and mixed, then molten into alloy state in an induction furnace. The molten alloy was ejected using gas pressure through a nozzle to a copper drum rotating at high speed to be quenched quickly with cooling speed being as high as $10^5$–$10^6$ K/sec. The cooled alloy was pulverized using a ball mill, and 99.7 g of powder with a particle size ranging from 40 to 300 mesh were obtained by sieving. 375 g of 20 wt.-% sodium hydroxide aqueous solution was charged into a 500 ml three-necked flask equipped with a thermometer and a stirrer, and the above powder was slowly added thereto. The mixture was stirred at 60° C. for 4 h, then the solid was washed with deionized water until neutral to give a powdery composite catalyst.

Example 3

A. Condensation

Under vacuum condition, feeding pumps for the above complex base catalyst, aniline and nitrobenzene were simultaneously switched on and adjusted to such flow rate as aniline 150 kg/h, nitrobenzene 30 kg/h and the complex base catalyst 200 kg/h. The aniline, nitrobenzene and complex base catalyst were continuously fed into a falling film reactor to be heated and allowed to condense. Condensation liquid in the falling film reactor was discharged from the bottom into a first reactor to proceed with condensing. Part of condensation liquid from the bottom of the first reactor was conveyed back to the falling film reactor via a circulating pump, forming a local circulating system. Ethanol vapor at 78–90° C. was used as the heat medium of the falling film reactor. Reaction temperature was controlled as 75° C., pressure was controlled as 0.008 MPa (absolute pressure) and flow rate of the circulating liquid was controlled as 1 m³/h. The reactants overflowed from the first reactor into a second reactor. The process conditions of the second reactor, such as operational temperature and pressure, were identical with that of the first reactor. The total residence time of the reactants in the falling film reactor, first reactor and second reactor was controlled as 5 h. Once the condensation reaction became stable, the complex base catalyst recovered according to the procedure as described below could be used, with only a minor amount of fresh complex base catalyst prepared according to example 1 being replenished, and the molar ratio of hydroxide ion to nitrobenzene in the reaction mixture was controlled not less than 1:1. The effluent of the second reactor was found to contain not larger than 0.1 wt.-% of nitrobenzene, 24.9 wt.-% of water and 16.1 wt.-% of 4-nitrosodiphenylamine and 4-nitrodiphenylamine.

B. Separation I

Thus obtained condensation liquid was continuously fed into the separation I process stage. To the condensation liquid subjected to filtering were introduced carbon dioxide and water until pH of the solution reaches about 8. The layers of system were separated, then calcium hydroxide was added at a rate of 25 kg/h to the obtained aqueous phase. After filtering, the obtained complex base catalyst was concentrated to its initial concentration, then conveyed back to the condensation process. The obtained organic phase contained 4-nitrodiphenylamine and 4-nitrosodiphenylamine.

C. Hydrogenation

The organic phase containing 4-nitrodiphenylamine and 4-nitrosodiphenylamine obtained by filtration in the separation I was fed to a first-stage hydrogenation reactor equipped with a sealed magnetic stirrer and a cooling and heating system. Hydrogen gas was used to replace the atmosphere of the system and pressurize to 1.3 MPa. A hydrogen gas circulator was switched on and flow rate of circulating hydrogen gas was maintained at 1 $Nm^3/h$. The circulating hydrogen gas was bubbled into the hydrogenation reactors to improve the gas-liquid mass transfer effect during reaction. The flow rate of the organic phase containing 4-nitrodiphenylamine and 4-nitrosodiphenylamine was controlled as 180 kg/h, and the flow rate of methanol was controlled as 48 kg/h. The powdery composite catalyst above-prepared was added simultaneously to the reactor so that the solid-liquid ratio by weight was 6:100. Hydrogenation-reduced liquid overflowed from the first-stage reactor into a second-stage reactor, then into a third-stage reactor, finally into a settler. The reaction temperature was 75–80° C., pressure was 1.3 MPa and total residence time was 5 h. The powdery composite catalyst was recovered as much as possible under the action of a magnetic separator. Solid-liquid mixture containing higher concentration of solid catalyst at the bottom of the settler was returned to the first-stage hydrogenation reactor via a Venturi type solid-liquid conveying device using the power of feeding stocks. The activity of the catalyst in the hydrogenation reaction was judged by monitoring the endpoint of reducing reaction, and thus it could be determined whether powdery composite catalyst for hydrogenation reaction was replenished.

The hydrogenation liquid was measured by high performance liquid chromatograph (HPLC) and was found not containing 4-nitrodiphenylamine and 4-nitrosodiphenylamine.

D. Separation II

The above hydrogenation liquid was conveyed to separation II process stage. The hydrogenation liquid was subjected to filtration to recover a minor amount of the powdery composite catalyst entrained in the hydrogenation liquid. The powdery composite catalyst recovered by filtration was recycled back to the hydrogenation process after regeneration.

The filtrate was fed at a flow rate of 228 kg/h to a methanol column, where methanol was obtained from column top and could be reused in the hydrogenation process. The bottoms was fed to an aniline column, where aniline was obtained from the column top and recycled back to the condensation process stage, and crude 4-aminodiphenylamine was obtained from column bottom. The aniline column was operated at a pressure of 0.005 MPa (absolute pressure), a column bottom temperature of 150 to 160° C., and a gas phase temperature of 115 to 125° C.

E. Refining

The crude 4-aminodiphenylamine from multiple sets of separation II equipment enters one set of refining equipment. The crude product of 4-aminodiphenylamine (containing 78.1 percent of 4-aminodiphenylamine, 21.75 percent of aniline, 0.05 percent of azobenzene and 0.1 percent of phenazine) was continuously fed to rectification column 1 at a flow rate of 120 kg/h via a gear pump. The temperature of still was controlled as 270° C., the temperature of column top was controlled as 110° C., vacuum degree was controlled as 0.094 MPa and reflux ratio was controlled as 5:1. Light components, i.e. aniline, azobenzene and phenazine, were taken out from the column top at a flow rate of about 26.2 kg/h, and conveyed to rectification column 3.

The rectification column 3 was operated at conditions of still temperature of 150° C., column top temperature of 90° C., vacuum degree of 0.094 MPa and reflux ratio of 1:1. Aniline was distilled off from column top at a flow rate of 24 kg/h, and azobenzene and phenazine were left in column bottom.

Bottoms of the rectification column 1 were conveyed to rectification column 2. The rectification column 2 was operated at conditions of still temperature of 280° C., column top temperature of 170° C., vacuum degree of 0.097 MPa and reflux ratio of 1:1. The finished 4-aminodiphenylamine was obtained at the column top of the rectification column 2.

Bottoms of the rectification column 2 were conveyed to batch still. The batch still was operated at conditions of kettle temperature of 285–320° C., vacuum degree of 0.094 MPa and top temperature of 235–250° C., to distill off the residual 4-aminodiphenylamine, which was recycled back to the rectification column 2 to be further distilled. The whole refining process of 4-aminodiphenylamine was continuously carried out. The finished 4-aminodiphenylamine product obtained had a purity of 99.1%, a melting point of 72° C. and a solidifying point of 72.4° C. The yield of the process in industrial scale production was 95.1%.

Example 4

4-Aminodiphenylamine was prepared according to the same procedure as described in Example 3 except that condensation was carried out as follows:

Under vacuum condition, feeding pumps for the complex base catalyst, aniline and nitrobenzene were simultaneously switched on and adjusted to such flow rate as aniline 150 kg/h, nitrobenzene 30 kg/h and the complex base catalyst 200 kg/h. The aniline, nitrobenzene and complex base catalyst were continuously fed into a falling film reactor to be heated and allowed to condense. Condensation liquid in the falling film reactor was discharged from the bottom into a first reactor to proceed with condensing. Part of condensation liquid from the bottom of the first reactor was conveyed back to the falling film reactor via a circulating pump, forming a local circulating system. Ethanol vapor at 78–90° C. was used as the heat medium of the falling film reactor. Reaction temperature was controlled as 75° C., pressure was controlled as 0.008 MPa (absolute pressure) and flow rate of the circulating liquid was controlled as 1 m³/h. The reactants overflowed from the first reactor into a second reactor. The process conditions of the second reactor, such as operational temperature and pressure, were identical with that of the first reactor. The total residence time of the reactants in the falling film reactor, first reactor and second reactor was controlled as 5 h. Once the condensation reaction became stable; the complex base catalyst recovered was used, with sodium hydroxide and tetraalkyl ammonium salt (i.e. tetramethylammnium carbonate according to Example 1) in a molar ratio of 1:1 being replenished, and the molar ratio of hydroxide ion to nitrobenzene in the reaction mixture was controlled not less than 1:1. The effluent of the second reactor was found to contain not larger than 0.1 wt.-% of nitrobenzene, 15.6 wt.-% of water and 17.6 wt.-% of 4-nitrosodiphenylamine and 4-nitrodiphenylamine.

Example 5

Process for Regenerating Catalyst 20 g of powdery composite catalyst, which was recovered by filtration of the hydrogenation liquid, was charged into a 100 ml three-necked flask equipped with a stirrer and a thermometer. 20 ml of 40% aqueous solution of sodium hydroxide was added thereto. While stirring, the mixture was heated to 90° C. and maintained at that temperature for 1 h. At the end of the reaction, the catalyst was subjected to ultrasonic washing for 30 min in a washing tank, followed by washing with water for multiple times until the pH of the washing water was 7–8. The gained solid was regenerated powdery composite catalyst.

Example 6

Preparation of a Complex Base Catalyst

To a 500 ml three-necked flask equipped with a condenser and a stirrer were added 230 g of water, followed by adding 91 g of pentahydrated tetramethyl ammonium hydroxide (containing 0.5 mol of tetramethyl ammonium hydroxide), 20 g (0.5 mol) of sodium hydroxide and 70 g of trimethyl hydroxyethyl ammonium chloride (0.5 mol). The mixture was homogeneously stirred at 75±2° C. to give a complex base catalyst having a concentration of 32.85 wt.-%.

Example 7

Preparation of a Complex Base Catalyst

To a 500 ml three-necked flask equipped with a condenser and a stirrer were added 230 g of water, followed by adding 91 g of pentahydrated tetramethyl ammonium hydroxide (containing 0.5 mol of tetramethyl ammonium hydroxide), 20 g (0.5 mol) of sodium hydroxide and 74.5 g of tetramethyl ammonium methylcarbonate ([(CH$_3$)$_4$N]$^+$[CO$_3$CH$_3$]$^-$) (0.5 mol). The mixture was homogeneously stirred at 75±2° C. to give a complex base catalyst having a concentration of 33.7 wt.-%.

Example 8

To a 500 ml four-necked flask equipped with a stirrer, a water segregator and a condenser were added 150 g of water, followed by adding 91 g of pentahydrated tetramethyl ammonium hydroxide (containing 0.5 mol of tetramethyl ammonium hydroxide), 20 g (0.5 mol) of sodium hydroxide and 74.5 g of tetramethyl ammonium methylcarbonate ([(CH$_3$)$_4$N]$^+$[CO$_3$CH$_3$]$^-$)(0.5 mol). Then 25 g of benzene were added thereto, and the mixture was heated to reflux. There were water layer and oil layer in the water segregator. Oil layer was returned to the four-necked flask and water layer was separated out until there was no water in distilled liquid. An anhydrous form of complex base catalyst was obtained.

Example 9

Preparation of Tetramethylammonium Methyl-carbonate ([(CH$_3$)$_4$N]$^+$[CO$_3$CH$_3$]$^-$)

To a 1.5 L autoclave equipped with a stirrer and a heating means were added 90 g (1.0 mol) of dimethyl carbonate, 59 g (1.0 mol) of trimethyl amine and 510 g (15 mol) of methanol. Stirring was initiated after the autoclave was sealed. The autoclave was heat to 140° C., and pressure was 1.5 MPa. The reaction was kept at 140° C. for 4 h. Then the reaction mixture was cooled to 50° C. and discharged into a 1 L three-necked flask. Part of methanol was removed from the solution of tetramethylammonium methyl-carbonate in methanol thus obtained under vacuum, and then the solution was cooled to ambient temperature. White crystal precipitated out. The crystal was filtrated, oven dried and recrystallized from methanol, to give 119.5 g of tetramethylammonium methyl-carbonate having a purity of 99.2% as measured by chromatography. The yield was 80.2%.

Example 10

92.5 g (1 mol) of 1-chloro-2,3-epoxy propane, 3 g (1 mol) of N-methyl diethanolamine, 2 g of sodium hydroxide and 700 g of water were charged into an autoclave with a stirrer, a heating means and a thermometric means. With stirring, the mixture was gradually heated to 120° C., then gaseous ethylene oxide was continuously passed into the autoclave to maintain a reactor pressure of 0.3 MPa until the quantity of ethylene oxide passed into reached 150 g. The reaction continued for further 2 h at that temperature, to give ClCH$_2$[CH$_2$CH$_2$O]$_{2-5}$—H. 60 g of gaseous trimethylamine were passed thereto. The autoclave was heat to 140° C., and pressure was 1.5 MPa. The reaction was maintained at that temperature for 4 h. Then the mixture was cooled to room temperature. After conventionally dehydrating and drying, 105 g of N,N,N-trimethyl-N-ethoxylated (1–4 moles of ethylene oxide) propyl ammonium chloride was obtained.

Example 11

Preparation of Tetramethyl Ammonium Hydroxide

To a 1.5 L autoclave equipped with a stirrer and a heating means were added 90 g (1.0 mol) of dimethyl carbonate, 59 g (1.0 mol) of trimethyl amine and 510 g (15 mol) of methanol. Stirring was initiated after the autoclave was sealed. The autoclave was heated to 140° C., and pressure was 1.5 MPa. The reaction was kept at 140° C. for 4 h. Then the reaction mixture was cooled to room temperature and discharged into a 1 L three-necked flask. A slurry consisting of 148 g (2.0 mol) of calcium hydroxide and 350 g of water was added thereto. Methanol was distilled off by heating over 8 h while stirring. 355 g of tetramethyl ammonium hydroxide solution was obtained after filtration. The content of tetramethyl ammonium hydroxide was found as 24.4% and the total reaction yield was 95.2%.

Example 12

Preparation of Tetraethyl Ammonium Hydroxide

To a 1.5 L autoclave equipped with a stirrer and a heating means were added 154 g (1.0 mol) of diethyl sulfate, 101 g (1.0 mol) of triethyl amine and 690 g (15 mol) of ethanol. Stirring was initiated after the autoclave was sealed. The autoclave was heat to 140° C., and pressure was 1.0 MPa. The reaction was kept at 140° C. for 4 h. Then the reaction mixture was cooled to room temperature and discharged into a 1 L three-necked flask. 80 g (2.0 mol) of sodium hydroxide was added thereto. The reaction mixture was heated at 45° C. for 4 h while stirring. After filtration, part of ethanol was distilled off from the filtrate. Then 500 g of water was added while ethanol was distilled off (part of water was entrained out), to give 604 g of tetraethyl ammonium hydroxide solution. The content of tetraethyl ammonium hydroxide was found as 23.3 wt.-% and the total reaction yield was 95.7%.

Example 13

Effect on Reaction Imposed by the Quantity of Aniline and Nitrobenzene

A local circulating system having a total volume of 1 L equipped with a vacuum system and a temperature control system was comprised of a miniature reactor, a film reactor and a circulating pump. The system was firstly filled with aniline, and the flow of the circulating pump was set at 2 l/h. A mixture, containing nitrobenzene, aniline and the complex base catalyst prepared according to example 1 at a molar ratio of nitrobenzene to aniline to OH⁻ in the complex base catalyst of 1:1:1.8, was fed to the reactor at a flow rate of 200 ml/h. The residence time was 5 h. The system temperature was maintained at 75° C. and the system pressure was maintained at 0.008 MPa (absolute pressure). After the aniline was replaced by reaction liquid and reaction liquid was stable in composition, a sample was taken and analyzed. Nitrobenzene was substantially not detectable. The reaction selectivity was calculated according to the total mole number of 4-nitrosodiphenylamine and 4-nitrodiphenylamine generated.

The results obtained under the same conditions except that the ratio of nitrobenzene to aniline was changed were showed in table 1.

TABLE 1

Effect on reaction imposed by the quantity of aniline and nitrobenzene

| No. | Nitrobenzene:aniline (mol/mol) | Reaction selectivity (%) |
|---|---|---|
| 1 | 1:1 | 90.2 |
| 2 | 1:3 | 96.1 |
| 3 | 1:5 | 99.1 |
| 4 | 1:10 | 99.3 |

It can be seen from the data showed in table 1 that increasing the molar ratio of aniline to nitrobenzene will enhance the reaction selectivity, increase target products and reduce the by-products. However, in the practice, if the quantity of aniline is too large, the loss of aniline and the energy consumption during separation will increase.

Example 14

Effect on Condensation Reaction Imposed by Water

A local circulating system having a total volume of 1 L equipped with a vacuum system and a temperature control system was comprised of a miniature reactor, a film reactor and a circulating pump. The system was firstly filled with aniline, and the flow of the circulating pump was set at 2 L/hr. A mixing liquid containing nitrobenzene, aniline and the complex base catalyst at a molar ratio of nitrobenzene to aniline to OH⁻ in the complex base catalyst of 1:7:1.15 was fed to the reactor at a certain flow. The system temperature was maintained at 75° C. and the system pressure was maintained at 0.008 MPa (absolute). After the aniline was replaced by reaction liquid and reaction liquid was stable in composition, the feeding flow rate of the reaction mixture was varied to adjust the residence time. The water contents of reaction effluent, measured when the measured content of nitrobenzene was equal to or less than 0.1% and calculated yield based on 4-nitrosodiphenylamine and 4-nitrodiphenylamine generated was 97%, were listed below.

| No. | Molar ratio of three components in complex base catalyst Tetramethyl ammonium hydroxide:N,N-dimethyl-N,N-bis(ethoxylated (1–4 moles of ethylene oxide) propyl) ammonium carbonate:sodium hydroxide | Water content in product (%) |
|---|---|---|
| 1 | 5:2:2 | 5.1 |
| 2 | 3:2:2 | 10.2 |
| 3 | 2:2:2 | 15.4 |
| 4 | 1:2:1 | 17.5 |
| 5 | 0.5:2:0.5 | 19.8 |
| 6 | Tetramethyl ammonium hydroxide is used as catalyst | 1.2 |

It can be seen that water content at the end of the reaction increases as the proportion of N,N-dimethyl-N,N-bis (ethoxylated (1–4 moles of ethylene oxide) propyl) ammonium carbonate in the complex catalyst increases. Namely, with the use of a complex base catalyst according to the present invention, the range of permitted water content in the reaction mixture at the end of reaction is greatly enlarged, that is, the yield is good enough even when there is a higher content of water in the reaction system. The less the water content is in the later phase of the reaction, the lower the dehydration efficiency is, thus reaction difficulty is reduced in the process according to the present invention. If only the tetramethyl ammonium hydroxide is used as catalyst, the yield cannot reach 97% until the water content of reaction mixture is reduced to 1.2% by dehydration, which imposes difficulty to the reaction control and increases the power consumption.

Example 15

Anhydrous complex catalyst prepared in example 8 and 651 g of aniline were charged into a four-necked flask with stirring device and thermometer. With stirring, the temperature was elevated to 75° C. and pressure was reduced to 0.008 MPa (absolute pressure). Aniline was returned to the four-necked flask after the water-aniline azeotrope is distilled until the water content in the system is less than 0.5%. 123 g of nitrobenzene was dropwise added over 2 h, then the dehydrating was continued for 4 h. It was found via chromatographic analysis that the yield of 4-nitrosodiphenylamine and 4-nitrodiphenylamine was 97.4% and the water content in the system was less than 0.5%.

Example 16

The Comparison of Continuous Film Reaction and Complete Mixing Reaction

Continuous film reactions and complete mixing reactions were conducted under the following conditions: molar ratio of aniline to nitrobenzene to OH⁻ in complex base catalyst was controlled at 7.5:1:1.5, reaction temperature was 75° C., reaction time was 5 h, and reaction pressure was 0.005 MPa (absolute pressure). Results were listed in Table 2 and Table 3.

TABLE 2

Results of complete mixing reactions

| No. | Conversion rate of nitrobenzene % | Yield % |
|---|---|---|
| 1 | 98.1 | 94.6 |
| 2 | 98.3 | 95.1 |
| 3 | 98.1 | 94.8 |

TABLE 3

Results of continuous film reactions

| No. | Conversion rate of nitrobenzene % | Yield % |
|---|---|---|
| 1 | 99.2 | 97.6 |
| 2 | 99.9 | 98.1 |
| 3 | 99.5 | 97.8 |

Example 17

Catalytic Hydrogenation in a Fixed Bed Reactor

A 400 ml of reactor was filled with copper catalyst in cylindrical shape having a diameter of 5 mm and a height of 5 mm. The catalyst contained 42% of copper oxide, 42% of zinc oxide, 6% of aluminum oxide and balance amount of physical water. Under a flow of hydrogen gas, the catalyst bed was activated at 110–240° C. for 24 hours. The organic phase containing 4-nitrosodiphenylamine and 4-nitrodiphenylamine obtained in separation I in Example 3 was molten by slightly heating and then mixed with methanol having a volume equal to 30% of the volume of the organic phase. The mixture, at a flow rate of 100 ml/h, was mixed with hydrogen gas and then preheated prior to being added to above hydrogenation reactor. The hydrogenation was performed at 135° C. under a pressure of 5.0 MPa with gas-liquid ratio being 1000:1. The hydrogenation-reduced liquid was measured by high performance liquid chromatograph (HPLC) and was found not containing 4-nitrodiphenylamine and 4-nitrosodiphenylamine. The unit was continuously operated under above conditions for 500 hours.

Example 18

Batch Hydrogenating Example 500 g of separation I liquid containing 17.5 weight percent of 4-nitrosodiphenylamine and 3.0 weight percent of 4-nitrodiphenylamine was charged into a 1 L autoclave with stirring device and temperature control device. 150 g of ethanol and 5 g of the powdery composite catalyst prepared in example 2 were added thereto. The system atmosphere was replaced with hydrogen gas for three times, and then the system was pressurized to 0.8 MPa. While stirring, the reaction mixture was heated to 100° C. and maintained at this temperature for 4 h. At the end of the reaction, the mixture was cooled, and then discharged after pressure release. The reaction liquid was analyzed via HPLC, and was found containing no 4-nitrosodiphenylamine and 4-nitrodiphenylamine but 14.6% of 4-aminodiphylamine (chromatograph content).

Comparison of Powdery Composite Catalyst and Noble Metal Catalyst

Pd/C catalyst with 5 wt. % of palladium was compared with the powdery composite catalyst according to the present invention. Experiments were carried out under the same conditions as described in above batch hydrogenating example. The quantities of catalysts used were identical, and both Pd/C catalyst and powdery composite catalyst were recovered and reused after the reaction. Within 21 times of reuse, 4-nitrosodiphenylamine was undetectable in both reaction liquids. However, at the twenty-first time of reuse, the reaction liquid obtained by using Pd/C catalyst was found containing 0.1 wt. % of 4-nitrodiphylamine while the reaction liquid obtained by using the powdery composite catalyst according to the present invention was found containing no 4-nitrodiphylamine. The results showed that the antitoxic performance of the powdery composite catalyst according to the present invention was better than that of the noble metal catalyst.

What is claimed is:

1. A process for preparing 4-aminodiphenylamine comprising the steps of
   i) reacting nitrobenzene and aniline in presence of a complex base catalyst in a condensation reaction to form a reaction mixture;
   ii) separating, recovering, and reusing the complex base catalyst;
   iii) hydrogenating the reaction mixture in presence of hydrogen, hydrogenation catalyst, and a hydrogenation solvent to obtain a hydrogenation reaction product;
   iv) separating, recovering, and reusing aniline and optionally the hydrogenation solvent from the hydrogenation reaction product;
   v) isolating and refining 4-aminodiphenylamine from the hydrogenation reaction product.

2. The process according to claim 1, wherein the condensation reaction step i) is carried out under conditions comprising a nitrobenzene to aniline molar ratio of about 1:1 to 1:15, reaction temperature of about 20 to 150° C., reaction pressure of about 0.005 to 0.1 MPa (absolute pressure), and reaction time of about 3.5 to 6 hours.

3. The process according to claim 1, wherein a molar ratio of hydroxide ion in the complex base catalyst to nitrobenzene is in a range of about 1:4 to 4:1.

4. The process according to claim 1, wherein said complex base catalyst comprises a tetraalkyl ammonium hydroxide, an alkali metal hydroxide, and a tetraalkyl ammonium salt.

5. The process according to claim 4, wherein a molar ratio of the tetraalkyl ammonium hydroxide to the alkali metal hydroxide to the tetraalkyl ammonium salt in the complex base catalyst is (0–9):(0.5–3):(0.5–3), and a sum of concentration of the tetraalkyl ammonium hydroxide, the alkali metal hydroxide, and the tetraalkyl ammonium salt ranges from 10 to 100 percent by weight.

6. The process according to claim 4, wherein the complex base catalyst is prepared by the steps of
   stirring and mixing the tetraalkyl ammonium hydroxide, the alkali metal hydroxide or alkali metal oxide, and the tetraalkyl ammonium salt in water at a temperature of from 0 to 90° C. to form a homogenous mixture of an aqueous form of the complex base catalyst, wherein the tetraalkyl ammonium hydroxide, alkali metal hydroxide or oxide, and tetraalkyl ammonium salt are in solid form or aqueous solution.

7. The process according to claim 4, wherein the complex base catalyst is prepared by the steps of stirring and mixing the tetraalkyl animonium hydroxide, alkali metal hydroxide or oxide, and tetraalkyl animonium salt in water at a temperature of from 0 to 90° C. until being homogeneous, completely removing water through azeotropic process from the homogeneous mixture by adding benzene to form an anhydrous complex base catalyst, wherein the tetraalkyl ammonium hydroxide, alkali metal hydroxide or oxide, and tetraalkyl animonium salt are in solid form or aqueous solution.

8. The process according to claim 4, wherein the tetraalkyl ammonium salt is represented by a general formula of

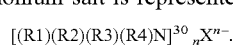

wherein R1, R2, R3 and R4, each of which may be identical or different, can be alkyl having from 1 to 4 carbon atoms, said alkyl being optionally substituted by a hydrophilic substituent; $X^{n-}$ is selected from the group consisting of halide ion, sulfate radical, carbonate radical, phosphate radical, bicarbonate radical, bisulfate radical, $C_1$–$C_2$-alkyl carbonate radical, $C_1$–$C_2$-alkyl sulfate radical; and n is a value of from 1 to 2.

9. The process according to claim 8, wherein at least one of R1, R2, R3 and R4 is substituted by a hydrophilic substituent selected from the group consisting of hydroxy, methoxy, polyether, cationic polyamide, polyester, polyethylene polyamine, and highly water-soluble quaternary ammonium salt-containing radical.

10. The process according to claim 8, wherein the tetraalkyl ammonium salt is a hydrophilic substituent-carrying tetraalkyl ammonium salt selected from the group consisting of poly-methylated triethylene tetraamine sulfate, poly-methylated diethylene triamine carbonate, N,N-dimethyl-N,N-bis(methoxyethyl) ammonium carbonate, N-methyl-N,N,N-tri(methoxyethyl) ammonium carbonate, N,N,N-trimethyl-N-hydroxyethyl ammonium carbonate, trimethyl hydroxyethyl ammonium chloride, N,N,N-trimethyl-N-ethoxylated (1–4 moles of ethylene oxide) ethyl ammonium carbonate, N,N,N-trimethyl-N-ethoxylated (1–4 moles of ethylene oxide) propyl ammonium carbonate, N,N,N-trimethyl-N-ethoxylated (1–4 moles of ethylene oxide) propyl ammonium chloride, and N,N-dimethyl-N,N-bis(ethoxylated (1–4 moles of ethylene oxide) propyl) ammonium carbonate.

11. The process according to claim 8, wherein the tetraalkyl ammonium salt is selected from the group consisting of tetramethyl ammonium carbonate, tetramethyl ammonium methyl-carbonate, tetraethyl ammonium carbonate, tetraethyl ammonium ethyl-carbonate, tetramethyl ammonium sulfate, tetramethyl ammonium methyl-sulfate, tetraethyl ammonium sulfate, and tetraethyl ammonium ethyl-sulfate.

12. The process according to claim 8, wherein the tetraalkyl ammonium salt is prepared by the step of reacting a trialkyl amine with a di($C_1$–$C_2$)alkyl carbonate or di($C_1$–$C_2$)alkyl sulfate in a polar solvent.

13. The process according to claim 12, which is undertaken under reaction conditions comprising a reaction pressure ranging from 0.1 to 3.0 MPa, a reaction temperature ranging from 50 to 200° C., a reaction time ranging from 1.5 to 6 hours, a molar ratio of trialkyl amine to di($C_1$–$C_2$)alkyl carbonate or di($C_1$–$C_2$)alkyl sulfate ranging from 2:1 to 1:2, the polar solvent is methanol, ethanol, or isopropanol, and the polar solvent is in an amount of from 1 to 10 times of weight of the trialkyl amine.

14. The process according to claim 1, wherein the condensation reaction of step i) is performed in the absence of oxygen.

15. The process according to claim 1, wherein the condensation reaction of step i) is performed without adding proton material or is performed without controlling proton material.

16. The process according to claim 1, wherein the condensation reaction of step i) is performed in the absence of a solvent.

17. The process according to claim 1, wherein the complex base catalyst is added at an initiation of the condensation reaction and only tetraalkyl ammonium salt, or alkali metal hydroxide or oxide, or both are replenished during the course of the reaction.

18. The process according to claim 1, wherein in step i), the condensation reaction is conducted in a circulating system comprising a condensing circulating pump, a falling film reactor, and a first reactor.

19. The process according to claim 1, wherein a falling film reactor is used in step i), and the falling film reactor employs a heat medium selected from the group consisting of ethanol vapor, hot water, steam, and methanol vapor.

20. The process according to claim 1, wherein in step ii), the complex base catalyst is recovered by neutralizing the reaction mixture with an acidic matter to form an aqueous phase, and basifying the aqueous phase using a base, wherein said acidic matter is selected from the group consisting of an inorganic acid, a combination of an oxide of the inorganic acid and water, and an inorganic acid salt, and wherein said base is selected from the group consisting of a hydroxide or oxide of alkali metal and alkaline earth metal.

21. The process according to claim 20, wherein the acidic material is selected from the group consisting of hydrochloric acid, sulfuric acid, nitric acid, carbonic acid, sodium bicarbonate, a combination of carbon dioxide and water, and a combination of sulfur trioxide and water.

22. The process according to claim 1, wherein the hydrogenation catalyst comprises an active component selected from the group consisting of a Group VIII element, Cu, Cr, Zn and Mn, and optionally a co-catalyst component.

23. The process according to claim 1, wherein the hydrogenation catalyst is a powdery composite catalyst.

24. The process according to claim 23, wherein said hydrogenation catalyst comprises nickel, aluminum, and a component A, said component A is at least one selected from the group consisting of Fe, Cu, Co, Mn, Cr, Mo, B, and P.

25. The process according to claim 24, wherein nickel is at a range from about 25 to 99.9 wt %, and a total of aluminum and the component A is at a range from about 0.1 to 75 wt %.

26. The process according to claim 1, wherein the step iii) hydrogenation reaction is carried out with hydrogen as reducing agent; a volume ratio of gas to liquid is in a range of from about 10:1 to 1500:1; a weight ratio of solid to liquid is in a range of from about 0.5:100 to 16:100 when a non-fixed bed hydrogenation process is used; and a weight ratio of solvent to step ii) condensation liquid from which the complex base catalyst has been separated in a range of from about 1:10 to 5:10;

wherein the liquid includes solvent and step ii) condensation liquid from which the complex base catalyst has been separated, and the solid represents the hydrogenation catalyst;

wherein step iii) hydrogenation reaction is carried out at a temperature of about 50 to 150° C., a pressure of about 0.2 to 6.0 MPa (absolute pressure), and a reaction time ranges from 2 to 7 hours.

27. The process according to claim 25, wherein the powdery composite catalyst is prepared by mixing powdery nickel, powdery aluminum, and the component A in the weight ranges to obtain a mixture, melting the mixture, pulverizing the melt mixture into powder after discharging and quenching, and treating the pulverized powder with an aqueous solution of a hydroxide.

28. The process according to claim 1, wherein a solvent for the hydrogenation reaction of step iii) is selected from the group consisting of an alcohol, water, and a mixture thereof.

29. The process according to claim 1, further comprising separating, recovering, and reusing the hydrogenation catalyst after the hydrogenation step iii), wherein the hydrogenation catalyst is optionally at least partially regenerated prior to being reused.

30. The process according to claim 23, wherein a magnetic separator is used to recover magnetic powdery composite catalyst at step iv).

31. The process according to claim 30, wherein the powdery composite catalyst is spent and regenerated by treating with ultrasonic vibration, or strong base, or both.

32. The process according to claim 30, wherein the recovered powdery composite catalyst is conveyed back to the hydrogenation step reactor via a Venturi tube.

33. The process according to claim 1, wherein the step v) refining is performed in a three-column continuous process and a batch rectification process, wherein column 1, 2, and 3 are operated at a pressure ranging independently from about 0.09 to 0.098 MPa; a still temperature of from about 260 to 290° C., from about 260 to 300° C., and from about 120 to 170° C., respectively; a reflux ratio of from about 2:1 to 10:1, from about 1:0.5 to 1:4, and from about 1:0.5 to 1:2, respectively; and the batch rectification column is operated at a pressure of from about 0.09 to 0.098 MPa, and a still temperature of from about 280 to 330° C.

34. A process for preparing 4-aminodiphenylamine comprising the steps of i) reacting nitrobenzene and aniline in presence of a complex base catalyst in a condensation reaction to form a reaction mixture comprising 4-nitrodiphenylamine and 4-nitrosodiphenylamine, said complex base catalyst comprising a tetraalkyl ammonium hydroxide, an alkali metal hydroxide, and a tetraalkyl ammonium salt;

ii) separating, recovering, and reusing the complex base catalyst;

iii) hydrogenating the reaction mixture in presence of hydrogen, hydrogenation catalyst, and a hydrogenation solvent to obtain a hydrogenation reaction product;

iv) separating, recovering, and reusing aniline and optionally the hydrogenation solvent from the hydrogenation reaction product;

v) isolating 4-aminodiphenylamine from the hydrogenation reaction product.

35. A process for preparing 4-aminodiphenylamine comprising the steps of:

(i) continuously feeding nitrobenzene, aniline, and a complex base catalyst to condensation reactor via metering pumps, and allowing them to react to form a condensation liquid containing 4-nitrodiphenylamine, 4-nitrosodiphenylamine, and salts thereof;

(ii) continuously feeding the condensation liquid to a separation I reactor, where the complex base catalyst is recovered by neutralizing the condensation liquid with an acidic material to conduct separation and obtain an aqueous phase, basifying the aqueous phase by a base, and recycling the recovered complex base catalyst to the condensation reactor;

(iii) continuously feeding liquid from the separation I reactor and a hydrogenation solvent to a hydrogenation reactor, and allowing to react with hydrogen gas in the presence of a powdery composite catalyst to form a hydrogenation liquid containing 4-aminodiphenylamine;

(iv) feeding the liquid from step iii) to a separation II reactor, where the powdery composite catalyst, which is to be recycled to the hydrogenation reactor directly or after being at least partially regenerated, aniline, which is to be recycled to the condensation reactor, and optionally, hydrogenation solvent, which is to be recycled to the hydrogenation reactor, are obtained;

(v) feeding crude 4-aminodiphenylamine, from which most of aniline has been separated in step iv), to a refining reactor, where aniline is recovered and recycled back to the condensation reactor and refined 4-aminodipheylamine is obtained.

* * * * *